(12) United States Patent
Long et al.

(10) Patent No.: US 6,642,281 B1
(45) Date of Patent: *Nov. 4, 2003

(54) FISCHER-TROPSCH PROCESS

(75) Inventors: David Chester Long, Baton Rouge, LA (US); Michel A. Daage, Baton, LA (US); Russell John Koveal, Baton Rouge, LA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/653,720

(22) Filed: Sep. 1, 2000

(51) Int. Cl.[7] .......................... C07C 27/00; B01J 20/34; B01J 23/40; B01J 23/72
(52) U.S. Cl. ..................... 518/709; 518/700; 518/706; 518/715; 502/20; 502/326; 502/331
(58) Field of Search ................................ 518/700, 706, 518/709, 715; 502/20, 326, 331

(56) References Cited

U.S. PATENT DOCUMENTS

| | | | | |
|---|---|---|---|---|
| 4,826,799 A | * | 5/1989 | Cheng et al. | 502/301 |
| 4,895,994 A | * | 1/1990 | Cheng et al. | 585/270 |
| 5,536,694 A | * | 7/1996 | Schuetz et al. | 502/301 |

* cited by examiner

Primary Examiner—Johann Richter
Assistant Examiner—J. Parsa
(74) Attorney, Agent, or Firm—Estelle C. Bakun

(57) ABSTRACT

There is provided an improved system and process for the catalytic hydrogenation of carbon monoxide to form a mixture of hydrocarbons utilizing a plurality of reactors in series. Synthesis gas entering the system under pressure is partially converted in at least one initial stage reactor and the effluent therefrom introduced into a final stage reactor. In the at least one initial stage reactor, a portion of the catalyst is continuously or periodically removed with some hydrocarbons and treated to renew, or renew and enhance it, and returned. The treatment comprises reducing the hydrocarbon context of the withdrawn mixture, heating to a temperature above at least one of the metals in the catalyst thereby forming a melt, removing any slag forming on the melt, cooling the melt and reducing the particle size of the resulting solid to a fine powder of renewed catalyst. The renewed catalyst may be treated to further enhance its properties by slurry low temperature oxidation or passivated before being returned to the at least one initial stage reactor. The final stage reactor, which has a catalyst of the same type or differing from that in the at least one initial stage reactor, receives a feed therefrom having a substantially reduced level of impurities, thereby enhancing the efficiency and longevity of the catalyst contained therein. The system can further employ at least one intermediate stage reactor configured so that all stages are operably connected in series and all reactors with a given stage are operably connected in parallel.

14 Claims, 1 Drawing Sheet

FISCHER-TROPSCH PROCESS

This invention relates to the production of higher hydrocarbons from synthesis gas by the Fischer-Tropsch process.

BACKGROUND OF THE INVENTION

The production of higher hydrocarbon materials from synthesis gas, i.e. carbon monoxide and hydrogen, commonly known as the Fischer-Tropsch process, has been in commercial use for many years. In such processes, the synthesis gas mixture is contacted with a suitable Fischer-Tropsch catalyst under shifting or non-shifting conditions, preferably the latter wherein little or no water gas shift takes place. Suitable Fischer-Tropsch catalysts comprise one or more Group VIII catalytic metals, such as iron, cobalt and nickel.

There exist many variations of the basic preparation of Fischer-Tropsch catalysts such as, for example, deposition of alloys onto a performed support by flame spraying, (U.S. Pat. No. 4,089,812), formation of the alloy by surface diffusion of aluminum on a non-leachable metal substrate (U.S. Pat. No. 2,583,619), and forming pellets from the powdered alloys for use in fixed bed reaction vessels (U.S. Pat. Nos. 4,826,799, 4,895,994 and 5,536,694, for example). The choice of a particular catalyst formulation, method of fabrication and method of activation depends in large measure on the catalytic activity, the desired product or products, whether or not the catalyst can be regenerated and the specific process components and configurations.

The production of hydrocarbons by the Fisher-Tropsch process may be carried out in virtually any type reactor, e.g. fixed bed, moving bed, fluidized bed, slurry, bubbling bed and the like. A preferred reactor carrying out such reactions is the slurry bubble column developed by Exxon Research & Engineering Company. This reactor, which is ideally suited for carrying out highly exothermic, three-phase catalytic reactions, is described in U.S. Pat. No. 5,348,982. In such reactors, the solid phase catalyst is dispersed or held in suspension in a liquid phase by a gas phase that continuously bubbles through the liquid phase. The catalyst loading in slurry bubble reactors can vary within a broad range of concentrations, but must remain short of the so-termed "mud limit" where the concentration of the catalyst reaches a level such that mixing and pumping of the slurry become so difficult as to render practical operation impossible. The use of high metal-loading catalysts or bulk metal catalysts is preferred in slurry bubble reactors in order to maximize the productivity of both catalyst and reactor.

Particularly suited for the production of hydrocarbons by Fischer-Tropsch synthesis from synthesis gas are Dispersed Active Metals ("DAM") which are primarily, i.e. at least about 50 wt. %, preferably at least 80 wt. %, composed of one or a mixture of metals such as described above and are, without further treatment, capable of catalyzing Fischer-Tropsch synthesis. DAM catalysts may be prepared by any of a number of art-recognized processes. An extensive review of processes of forming DAM catalysts can be found in "Active Metals", Edited by Alois Furstner, published by VCH Verlagsgesellschaft mbH, D-69451 Weinheim (FRG) in 1996 and the references cited therein. Methodologies described therein include the Rieke method, the use of ultrasound, reduction of metal salts, colloids, nanoscale cluster and powders. Other relevant references include, for example, the preparation of amorphous iron catalyst by high intensity sonolysis of iron pentacarbonyl, Suslick et al., Nature, Vol. 353, pp. 414–416 (1991) and the formation of single domain cobalt clusters by reduction of a cobalt salt with hydrazine, Gibson et el., Science, Vol. 267, pp. 1338–1340, (1998). Finally, intermetallic alloys, particularly those known for forming metal hydrides, such as $LaCo_5$, can be formed into a fine powder by the application of hydrogen adsorption/desorption cycles. DAM catalysts can also be prepared by thermal or chemical decomposition of metal formates or oxalates. These methods are given as examples and are not intended in any way to limit the term "DAM" as utilized in the context of the present invention.

There are many well-known methods for the preparation of DAM catalysts in the literature. In 1924, M. Raney prepared a Nickel hydrogenation catalyst by using a process known today as the Raney Process and Raney catalysts. Such catalysts are described and illustrated, for example, in U.S. Pat. No. 4,826,799. The process of preparing these catalysts is, in essence, forming at least a binary alloy of metals, at least one of which can be extracted, and extracting it leaving a porous residue of the non-soluble metal or metals that possesses catalytic activity. These groups of metals are well known to those skilled in the art. The residue catalyst metals include Ni, Co, Cu, Fe and the Group VIII noble metals. The leachable or soluble metal group includes aluminum, zinc, titanium or silicon, typically aluminum. Once the alloys are formed, they are ground to a fine powder and treated to extract the leachable metal, typically with strong caustic, such as sodium hydroxide. Alternatively, the alloy is formed onto or impregnated into a suitable rigid support structure which is then extracted with caustic to form a porous, supported catalyst.

The high metal content of DAM catalysts, i.e. at least 50% metal, represents a major economic impediment to their use unless low cost recovery technology can be implemented as well. Those of ordinary skill in the art are aware that metals constituting DAM catalysts, particularly Raney catalysts, are conventionally recovered by subjecting the used, or spent, catalysts to multiple processing steps, principally for the purpose of purification of the metal. The particular methodology chosen to purify and recover the metal depends in large measure on the nature of the impurities and contaminants that have been deposited on the catalyst during use. In most applications, drastic treatments are required because of significant contamination of the metals by one or more of carbonaceous deposits, heteroorganic compounds, i.e. compounds containing sulfur and/or nitrogen, and other metals.

Typically, spent DAM catalysts are treated in the reactor by oxidation to permit safe unloading and shipping to a metal processing facility. The oxidation can be carried out, for example, by air oxidation of the catalyst slurry, or by treatment with bleach as recommended by catalyst manufacturers. In the metal processing facility, the catalysts are generally roasted in air, dissolved in strong acid and the different metals selectively reprecipitated in the form of salts. The metals may be reused in the form of the salts, or converted back into metallic form, depending on the requirements of the synthesis. Such treatments must be effective and efficient because, although carbon monoxide hydrogenation processes are conducted in an exceptionally clean environment, DAM catalysts are generally sensitive to comparatively minor amounts of contaminants.

Those of ordinary skill in the art recognize that the economic worth of a given catalyst is a function of its original cost, its value as a spent catalyst, e.g. for regeneration of fresh catalyst, its activity and its half-life in the reactor. Another important aspect of the value of a catalyst is its selectivity which is the ratio of the percent of feed material converted to desired higher hydrocarbons to that of short chain hydrocarbons produced, primarily methane, commonly referred to as "methane selectivity". It will be appreciated that a process that will effectively extend the useful life of a catalyst before it must be disposed of through conventional metal recovery will significantly improve the value of that catalyst. In accordance with the present invention, an improved Fischer-Tropsch process is provided wherein a plurality of reactors is utilized to process incoming synthesis gas with enhanced efficiency in terms of the activity and methane selectivity of a catalyst and, therefore, the overall efficiency of the process.

SUMMARY OF THE INVENTION

In accordance with the present invention, Fischer-Tropsch synthesis of higher hydrocarbons from synthesis gas is carried out in a system comprising a plurality of reactors operably connected in series comprising at least one initial stage reactor and a final stage reactor, wherein the catalyst in the at least one initial stage reactor is periodically or continuously renewed by withdrawing a mixture of hydrocarbons and a portion thereof, reducing the hydrocarbon content of the mixture, forming a melt by heating to the melting temperature of at least one of the metals in the catalyst, removing any slag that forms on the melt, cooling the melt to solidify it, reducing the particle size of the solid to a fine powder catalyst and returning at least a portion thereof to the at least one initial stage reactor. Wherein the catalyst in the at least one initial stage reactor is a Raney catalyst, a leachable metal is added to either the reduced hydrocarbon catalyst mixture or the melt and the solid formed by cooling the melt is comminuted to a fine powder and then extracted with caustic.

The renewed catalyst may be treated to further enhance its activity and selectivity by slurry low temperature oxidation and may also be passivated before being returned to the at least one initial stage reactor. The treatment of the catalyst in the at least one initial stage reactor according to the subject process permits a maximum productivity catalyst in the final stage reactor to operate at high efficiency for extended periods of time because the impurities it would ordinarily be exposed to are minimized. Depending on the catalyst in the final stage reactor, the catalyst withdrawn from the at least one initial stage reactor and renewed may be at least partially fed into the final stage reactor. A DAM catalyst in the final stage reactor may be enhanced by slurry low temperature oxidation and either replaced into the final stage reactor or recycled into the at least one initial stage reactor. In a further embodiment, there is at least one intermediate stage reactor that may receive renewed catalyst from the at least one initial stage reactor and recycle catalyst thereto. Wherein the catalyst in the final stage reactor is a DAM catalyst, further embodiments encompass variations for catalyst renewal, enhancement and recycle.

BRIEF SUMMARY OF THE DRAWING

The FIGURE (FIG. 1) is a block diagram illustrating the process of the present invention utilizing one initial stage reactor and one final stage reactor.

DETAILED DESCRIPTION OF THE INVENTION

Figure 1:
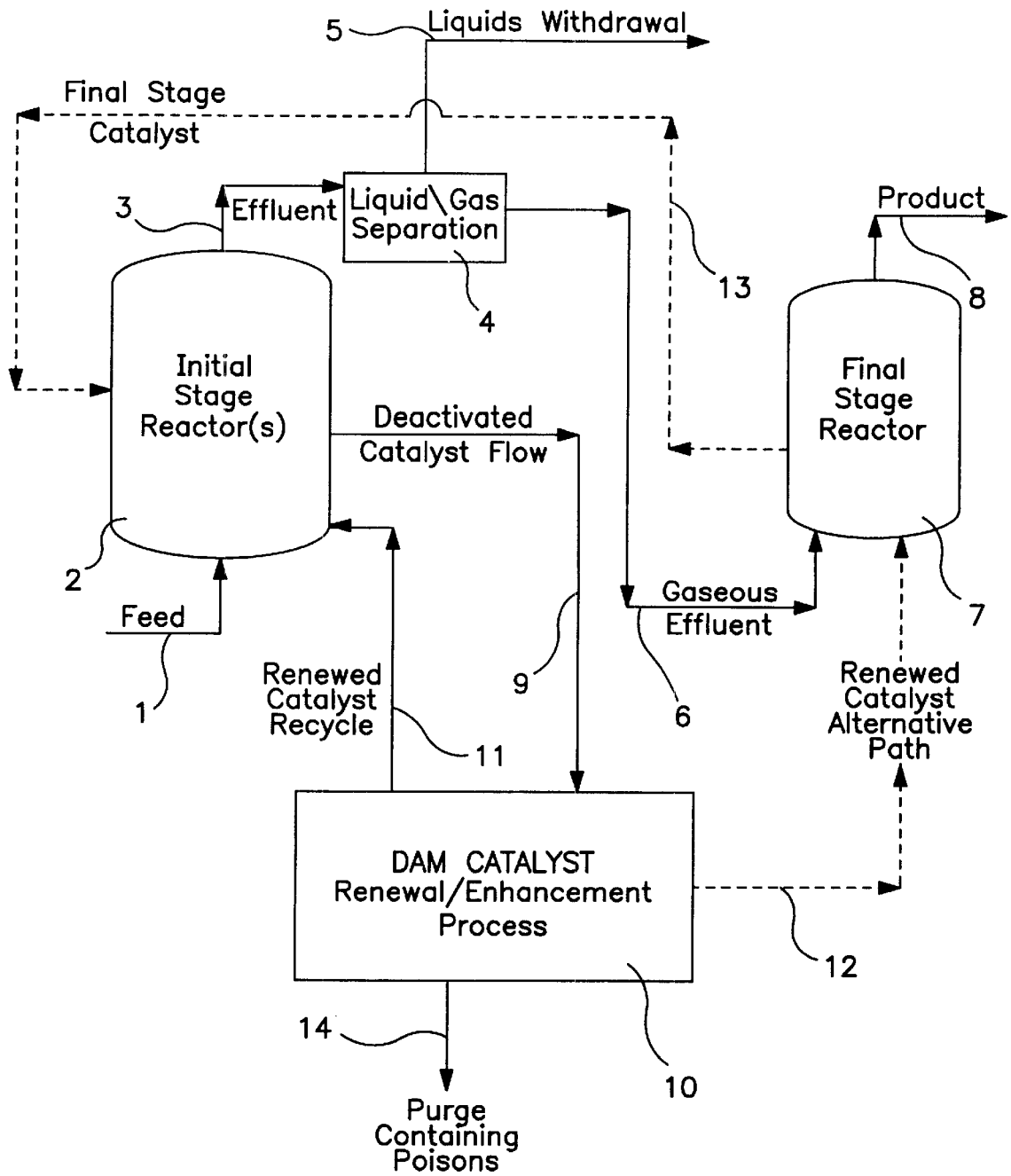

Dispersed Active Metals (DAM), which correspond essentially to reduced metals, are utilized in a broad range of applications such as the hydrogenation of fats and specialty chemicals. Start-up procedures, which may include specific activation sequences, are highly dependent upon the catalytic reaction, the process design and, in particular, the reaction vessel design and configuration. The slurry bubble column discussed above is a preferred vessel for carrying out carbon monoxide hydrogenation reactions and also for catalyst enhancement in accordance with the present invention. In such reactors, the solid phase catalyst is dispersed or held in suspension in a liquid hydrocarbon phase by a gas phase, which continuously bubbles through the liquid phase. DAM catalysts useful for such applications have a metallic content of at least 50 wt. %, preferably at least 80 wt. %, in the reduced metallic form. Preferred catalysts include intermetallic alloys or Raney catalysts, for example Raney cobalt. Among the intermetallic alloys, preferred examples are those suitable for forming metal hydrides, such as $LaCo_5$. Most preferably, the DAM catalyst comprises one or more of Co, Ru, Fe and Cu.

Catalysts most suited for use in slurry column reactors vessels typically are in a finely particulate form having an average diameter ranging from 1 to 1,000 lm, preferably from 10 to 500 lm, most preferably from 20 to 100 lm. The use of high metal loading catalysts and/or bulk catalysts is preferred in order to maximize the productivity of the reactions. The present process may be applied to other conventional reaction vessels known in the art wherein the catalyst is not immobilized, such as fluidized bed, slurry, bubbling bed and the like. In such moving bed reactors, contaminated catalyst would typically be withdrawn from the bottom of the vessel and catalyst that had been enhanced in accordance with the present process would be replaced at the top.

In the carbon monoxide hydrogenation reaction, a syngas feed comprising a mixture of hydrogen and carbon monoxide is bubbled up into the reactive hydrocarbon-containing slurry in which it is catalytically converted into liquid and gaseous products, preferably liquid hydrocarbons, with shifting or non-shifting conditions, preferably the latter, wherein little or no water/gas shift takes place. This hydrocarbon synthesis ("HCS") process is generally carried out at temperatures of from about 160° C. to 260° C., pressures of from about 5 atm to about 100 atm, preferably from 10 atm to 40 atm, and gas space velocities of from about 100V/Hr/V to about 40,000V/Hr/V, preferably from about 1,000V/Hr/V to about 15,000V/Hr/V, expressed as standard volumes of the gaseous carbon monoxide and hydrogen mixtures (25° C., 1 atm.) per hour per volume of catalyst, respectively. By volume of catalyst is meant packed bed volume including inter- and intra-particle volume. The stoichiometric ratio of hydrogen to carbon monoxide is about 2.1:1 for the production of higher hydrocarbons. This ratio can vary from about 1:1 to 4:1, preferably from 1.5:1 to 2.5:1, more preferably from 1.8:1 to 2.2:1. These reaction conditions are well known and a particular set of reaction conditions can readily be determined from the parameters given herein. The hydrocarbon-containing products formed in the process are essentially free of sulfur and nitrogen-containing contaminants.

The hydrocarbons produced in a process as described above are typically upgraded to more valuable products by subjecting all or a portion of the C5+ hydrocarbons to fractionation and/or conversion. By "conversion" is meant one or more operations in which the molecular structure of at least a portion of the hydrocarbon is changed and includes both non-catalytic processing, e.g. steam cracking, and catalytic processing, e.g. catalytic cracking, in which the portion, or fraction, is contacted with a suitable catalyst. If hydrogen is present as a reactant, such process steps are typically referred to as hydroconversion and variously as hydroisomerization, hydrocracking, hydrodewaxing, hydrorefining and the like. More rigorous hydrorefining is typically referred to as hydrotreating. These reactions are conducted under conditions well documented in the literature for the hydroconversion of hydrocarbon feeds, including hydrocarbon feeds rich in paraffins. Illustrative, but non-limiting, examples of more valuable products from such feeds by these processes include synthetic crude oil, liquid fuel, emulsions, purified olefins, solvents, monomers or polymers, lubricant oils, medicinal oils, waxy hydrocarbons, various nitrogen- or oxygen-containing products and the like. Examples of liquid fuels includes gasoline, diesel fuel and jet fuel, while lubricating oil includes automotive oil, jet oil, turbine oil and the like. Industrial oils include well drilling fluids, agricultural oils, heat transfer oils and the like.

The syngas utilized in carbon monoxide hydrogenation as described herein may be formed by various means known to those of ordinary skill in the art, such as a fluid bed syngas-generating unit as is disclosed, for example, in U.S. Pat. Nos. 4,888,131, and 5,160,456. Regardless of the source, syngas typically contains chemical species, such as ammonia and hydrogen cyanide, that will, over time, cause deactivation of the catalyst. Other deactivating chemical species may be formed during the carbon monoxide hydrogenation process itself. Those skilled in the art are aware of the fact that deactivation by those contaminants is generally reversible and the catalyst can be rejuvenated by treatment with hydrogen. However, catalyst deactivation that cannot be rejuvenated can be caused by the formation of refractory carbonaceous residues and/or permanent poisons such as sulfur, phosphorus, halides and other metal contaminants, as well as the build-up of fines in the reactor. Although the criteria for what are classified as fines particles may vary with the reactor, generally fines are recognized as particles smaller than 10 microns.

The process for carrying out Fischer-Tropsch synthesis of higher hydrocarbons in accordance with the present invention represents a significant improvement in efficiency in comparison to conventional processes. In the present process, a plurality of reactors is employed comprising at least one initial stage reactor and a final stage reactor connected in series. The use of more than two initial stage reactors for each final stage reactor is within the scope of the present invention. Typically, at least two initial stage reactors will be utilized for each final stage reactor. It will be appreciated that, where there is at least one intermediate stage reactor in the process of the invention as discussed below, there will be two initial stage reactors for each intermediate stage reactor and, typically, two intermediate stage reactors for each final stage reactor as well. Where a plurality of reactors is utilized for any stage of the system of the present invention, the reactors within a given stage are operably connected in parallel.

Although the reactors utilized in the system of the present invention may be any conventional reactor configuration, it is preferred as stated above that it be effected with slurry bubble column reactors. It has been found that, regardless of the type of reactor employed, utilization of a plurality of reactors in the present process significantly enhances the useful life of the catalysts employed and the overall efficiency of the process. In accordance with the present invention, a mixture of hydrocarbon, typically molten wax, and a portion of the catalyst is withdrawn from the at least one initial stage reactor in the system utilized to carry out applicants' process. While the amount of catalyst removed can vary within a rather wide range, it will be recognized that there must always be sufficient catalyst in the reactor to sustain the desired level of production. Generally, from about 0.01 wt. % to about 10 wt. % of the catalyst will be withdrawn from a given reactor at a given point in time during production. It is not intended that such amount of catalyst be removed in a single quantity. Rather, portions of the withdrawn catalyst will be at various stages of the renewal process as described below at any given time so that, when a portion is returned to or replaced in the reactor, an estimated like amount can be withdrawn. This holds true regardless of whether catalyst is returned to a single stage reactor or reactors, or recycled among two or three stages as will be described below.

Since a reactor will typically run for a considerable period of time before sufficient contaminants and/or fines accumulate to require implementing the renewal or enhancement of the catalyst as described herein, after it is calculated that substantially all of the catalyst in a reactor has been renewed or enhanced, it may again be operated for a period of time before re-commencing the treatment. However, it is preferred to carry out the process of renewing the catalyst in the at least one initial stage reactor continuously once it is initiated. While it would in theory be possible to stop the reactor to renew the catalyst as described herein, there would be no practical merit in doing so since it can be effectively carried out during production. The catalyst withdraw from the at least one initial stage reactor may be replaced with recycled renewed catalyst, with catalyst withdrawn from the final stage reactor when it contains a DAM catalyst, or with fresh catalyst so that efficient production is continuously maintained.

Turning to the FIGURE, it will be seen that, in the system of the present invention, syngas feed (1) is introduced into the at least one initial stage reactor (2), which effectively functions to carry out both a portion of the synthesis thereon and to remove a substantial portion of the impurities therefrom. This permits a high productivity catalyst to efficiently operate in the final stage at high activity and low methane selectivity for extended periods of time. In a system containing two initial stage reactors, not illustrated, they would be connected in parallel and the feed gas would be introduced into both. An effluent line (3) is withdrawn from the at least one initial stage reactor and subjected to cooling and liquid/gas separation procedures (4) resulting in liquids that are withdrawn (5) and residual gas (6) that is introduced into the final stage reactor. In the final stage reactor (7), the conversion of an optimum percentage of the feed gas is carried out and the resultant product (8) withdrawn as shown.

The operating conditions for the at least one initial stage reactor and final stage reactor may be set at values typical for hydrocarbon synthesis, preferably from about 10 to 40 atm. pressure and from 170° C. to about 260° C. It is preferred that the at least one initial stage reactor is operated at a temperature higher than the final stage reactor, i.e. the at least one initial stage reactor will be run at from about 230° C. to about 260° C., whereas the final stage reactor will be operated at from about 200° C. to about 230° C. The synthesis in the at least one initial stage reactor may be carried out in the presence of poisons such as hydrogen cyanide, carbon oxysulfide and ammonia that may be introduced with the feed gas, and possibly trace amounts of hydrogen sulfide. In the at least one initial stage reactor, these poisons are effectively removed and retained by the catalyst. In the system of the present invention, at least 30%, preferably from about 35 to 85% of the syngas feed is converted to product. The operation of the initial stage reactors in this manner makes possible the elimination of the cyanide converter typically utilized on Fischer-Tropsch reactors, a significant cost savings.

The catalyst in the final stage reactor may be the same as or different than that in the at least one initial stage reactor. The final stage reactor receives the effluent from the at least one initial stage reactor, which has gone through gas/liquid separation and had liquids withdrawn therefrom, substantially free of catalyst poisons. Hence, the hydrocarbon products formed therein are essentially free of sulfur and nitrogen-containing contaminants. Typically, the final stage reactor will operate with a high activity Raney-type or another conventional catalyst having a high metal content, for example a Co/Re/Ti catalyst, or a conventional supported cobalt catalyst. In the system of the present invention, there may also be at least one intermediate stage reactor, not shown, that would receive feed from the at least one initial stage reactor, convert another percentage thereof and deliver the remainder of the feed, now highly purified, to the final stage reactor. The catalyst in the at least one intermediate stage reactor is preferably the same as that in the at least one initial stage reactor. Wherein the catalyst in the final stage reactor is a high activity Raney-type or other conventional catalyst different than that in the at least one initial stage reactor, even though the feed coming in is exceptionally clean, at some point in the operation, it will be necessary to shut down the final stage reactor for cleaning and catalyst replacement. A decided advantage of the present invention is that the interval between such shut-downs is significantly extended due to the overall efficiency of the system.

Returning to the FIGURE, deactivated catalyst is withdrawn (9) from the at least one initial stage reactor, renewed (10) and at least a portion returned (11) thereto. A purge containing poisons (14) can be removed from the renewal/enhancement process (10). The renewal of the catalyst from the at least one initial stage reactor is carried out according to a process disclosed and claimed in copending application in the disclosure of which is incorporated herein by reference. In this process, the catalyst-hydrocarbon mixture withdrawn from the reactor is initially treated to reduce its hydrocarbon content. This may be carried out by one or more of several techniques. For example, separation may be effected by gravitational or centrifugal separation that allows the hydrocarbon to be decanted or removed by filtration, all of which require the hydrocarbons to be in a fluid state. The mixture may also be treated with a solvent or supercritical fluid that effectively weakens the interaction of the hydrocarbon with the catalyst surface so that the liquid and solid phases can readily be separated in the same manner. Suitable solvents include, for example, paraffin solvents or naphthas, alcohols, and aromatic solvents. Supercritical fluids include, for example, carbon dioxide, light paraffins and cyclopropane. Another means of reducing the hydrocarbon content of the mixture is to contact it with a hydrogen-containing gas at a temperature at least 20° C., preferably at least 50° C. higher than that of the reactor. Typically, the hydrogen pressure would be from atmospheric to about 1000 psi, preferably from 10 to 400 psi. The mixture may also be contacted with an oxygen-containing gas or steam at elevated temperature to effectively reduce the hydrocarbon content.

A plurality of the foregoing methodologies for reducing the hydrocarbon content of the mixture may be utilized sequentially in any order. A combination of the above-described methodologies would be employed because the hydrocarbon product is both liquid and solid. For example, for a mixture containing from 1 to 50%, typically from 2 to 40%, of wax, physical separation, i.e. centrifugation/decanting or filtration to remove liquid hydrocarbon, may advantageously be combined with treatment with hydrogen-containing gas at elevated temperature to dewax the catalyst particles as described above. The duration of the dewaxing treatment is adjusted to produce a residual carbon content of less than 5 wt. %, preferably less than 2 wt. %.

The reduced hydrocarbon mixture is converted to a DAM metal or metal alloy precursor. The first step in the conversion is heating above the melting point of at least one of the metals therein in a non-oxidizing atmosphere, preferably a reducing atmosphere, for a time sufficient to form a melt. This heating step will remove substantially all of the non-metallic contaminants, such as carbon and sulfur, by the formation of volatile compounds. This heating step is particularly advantageous to DAM catalysts that are substantially comprised of the metal or alloy themselves whereas, in contrast, such temperatures would be detrimental to conventional supported catalysts as their structure, morphology or physical integrity would be irreversibly destroyed. Any refractory metal oxides present can be separated or removed as a slag that floats on the surface of the melt. Other reducible metal contaminants, typically including but not limited to iron and nickel, that may have deposited on the surface of the catalyst, become redistributed into the bulk of the metal melt during the heating step, thus materially decreasing their concentration on the catalyst surface and, therefore, their detrimental effect. These metals, in the presence of carbon monoxide, have the capability to form metal carbonyls that have a negative effect on the efficacy of the catalyst. If an inordinately large amount of sulfur is present in the catalyst as a contaminant, methodologies typically utilized in the steel industry to enhance sulfur removal are typically employed. Such measures include the addition of a basic slag, for example, calcium oxide, calcium hydroxide, calcium carbonate, dolomite or, preferably, calcium magnesium silicate. A slag fluidity enhancer, such as calcium fluoride, may be added to enhance sulfur removal as well as the removal of refractory oxides. Temperatures in the range of 1,500° C. to 1,600° C. may further enhance the purification process.

The melt is then cooled and/or quenched by conventional techniques to form a solid mass which is then treated to reduce the particle size thereof to a fine powder of renewed catalyst. For metal-hydride derived DAM catalysts, this is carried out by conventional multiple hydrogen absorption/desorption cycles. The hydrogen absorption/desorption cycles applied to the metal hydride catalyst fulfill simultaneously both the requirements for dividing it into a fine powder and obtaining a metal hydride, corresponding to the DAM catalyst.

Wherein the DAM catalyst is a Raney type, e.g. a cobalt catalyst, a leachable metal such as aluminum, titanium, silicon or zinc, preferably aluminum, is added to the melt under a non-oxidizing atmosphere and the temperature maintained for a time sufficient to assure thorough mixing of the melt. Alternatively, metallic aluminum can be added to the mixture withdrawn from the reactor, or the reduced hydrocarbon mixture and the resulting mixture ignited, such as with an oxy-flame or electrical arc, to form a DAM metal or metal alloy precursor and a slag as described above which can be removed before further processing. In a preferred embodiment, the leachable metal is added to the reduced hydrocarbon content mixture prior to forming the melt. Following removal of any slag that has formed, the melt is cooled or quenched as above. The resulting solid is then treated by physical comminuting, i.e. crushing or grinding, to a reduced particle size, typically having an average particle size of from about 1 to 500 microns, preferably from 20 to 150 microns. The renewed Raney metal or DAM catalyst is then obtained by extraction of the leachable metal with alkali, preferably a concentrated aqueous solution of sodium hydroxide. Any of the various extraction methods available in the literature may be utilized to remove the leachable metal. Any fines resulting from the comminuting step are removed by physical separation, i.e. screening, and can be recycled to a subsequent melt.

The renewed DAM catalyst particles, which have a significant portion of their original activity restored, are then at least partially returned to the at least one initial stage reactor as described above. This may be carried out by forming a slurry of the DAM particles in liquid hydrocarbon, conveniently the hydrocarbon mixture withdrawn from the reactor to initiate the process from which the catalyst had been separated, or by suspending the particles in a non-oxidizing gas, preferably a reducing gas, or by gravity or pressure gradient, or any combination thereof. Preferably, the catalyst particles may be further enhanced prior to be returned to the reactor by slurry low temperature oxidation as described above to form an oxidized catalyst precursor that is a mixture of metallic and oxidic species. The oxidized catalyst precursor particles are treated to reform the active catalyst by reduction with hydrogen-containing gas at temperatures of from about 200° C. to 600° C., preferably from about 300° C. to 450° C., most preferably from about 340° C. to 400° C. Hydrogen partial pressure during the reduction would range from about 1 to 100 atmospheres, preferably from about 1 to 40 atmospheres.

In a further preferred embodiment of the subject process, prior to being returned to the at least one initial stage reactor, the catalyst particles are passivated by contacting them with a gas containing carbon monoxide, or carbon monoxide and hydrogen, under conditions such that carbon monoxide does not significantly decompose and is not hydrogenated to a material degree. Such conditions, for example, would be a temperature below about 150° C., preferably between about 25° C. and 100° C., and pressure below about 20 atm, particularly between about 1 and 10 atm. Those of ordinary skill in the art will appreciate that some decomposition or hydrogenation, respectively, of the carbon monoxide may take place regardless of the precautions taken by the operator. Hence, by "significantly" is meant that such decomposition/hydrogenation does not exceed 5% by volume of the feed gas. It has been found that catalysts that have been passivated in this manner typically exhibit higher initial carbon monoxide hydrogenation activity than similar, but unpassivated, catalysts. Other passivating agents include, for example, traces of oxygen or carbon dioxide.

In another embodiment of the catalyst treatment, the DAM catalyst withdrawn from the at least one initial stage reactor is renewed and is also treated to modify and/or enhance the properties thereof. This may be effected by the addition of one or more metal or metal compounds chosen among, without limitation, those active for carbon monoxide hydrogenation per se or for promoting either the activity or the selectivity of the catalyst. Suitable metals include, for example, Group VIII metals, Mo, W, Cu, Si, Cr, Ti, Mg, Mn, Zn, Hf, Al, Th and the like. The metal or metal compounds may be added to the hydrocarbon/catalyst mixture before the formation of the melt, or to the melt itself, as described above.

All or a portion of the active DAM catalyst particles are treated as described may be returned to the at least one initial stage reactor, or passed to the final stage reactor when the catalyst therein is of the same type as that in the at least one initial stage reactor. The FIGURE illustrates an alternate catalyst flow (12) whereby catalyst withdrawn from the at least one initial stage reactor and renewed is fed into the final stage reactor. The renewed catalyst may be only partially fed into the final stage reactor with the balance being returned to the initial stage reactor(s) as shown. The splitting of the renewed catalyst typically will occur where a plurality of initial stage reactors is utilized with a single final stage reactor, or where there are only two reactors, but the initial stage reactor is much larger than the final stage reactor. To compensate for the catalyst being fed into the final stage reactor, catalyst is withdrawn therefrom and returned to the at least one initial stage reactor as illustrated in (13) of the FIGURE. Catalyst withdrawn from the final stage reactor may be fed directly into the at least one initial stage reactor, or may be enhanced by slurry low temperature oxidation as described above, but not shown in the FIGURE, preferably with passivation, prior to being introduced into the at least one initial stage reactor. In another embodiment of the invention, catalyst withdrawn from the final stage reactor and enhanced as described above is returned to it, and the catalyst withdrawn from the at least one initial stage reactor and renewed is returned thereto.

The system of the present invention can further include at least one intermediate stage reactor that is connected in series between the at least one initial stage reactor and the final reactor and that is operated at conditions intermediate to those given above for the at least one initial stage reactor and final stage reactor, respectively. The effluent stream withdrawn from the at least one intermediate stage reactor undergoes cooling and gas/liquid separation procedures as described above to produce a second liquid stream that is withdrawn, and a feed stream of very high purity that is introduced into the final stage reactor. The presence of the at least one intermediate stage reactor gives rise to a number of additional embodiments of the system of the invention encompassing various flow paths for recycle, renewal and/or enhancement of the catalyst. Wherein the catalyst in the final stage reactor is different than that in the at least one initial stage reactor and the at least one intermediate stage reactor, it will not be recycled into either of the preceding upstream reactors, but may instead be recycled into the final stage reactor. It will be appreciated by those of ordinary skill in the art that the presence of the at least one intermediate reactor permits operation of the final stage reactor for even longer periods of time between shut-downs.

Wherein the catalyst in the final stage reactor is different from that in the other reactors, catalyst withdrawn from the at least one initial stage reactor and renewed may be at least partially introduced into the at least one intermediate stage reactor in the same manner as described above with regard to the final stage reactor. The remainder will be recycled into the at least one initial stage reactor. Further, catalyst withdrawn from the at least one intermediate stage reactor may be recycled to the at least one initial stage reactor as described above with regard to the two stage system. Preferably, such catalyst will be enhanced as described above before being introduced into the at least one initial stage reactor. Lastly, catalyst withdrawn from the at least one initial stage reactor may be recycled thereto and that withdrawn from the at least one intermediate stage reactor may be recycled thereto as well.

A further group of embodiments is realized wherein the catalyst in the final stage reactor is the same as the preceding two stages. In this instance, at least a portion of the catalyst withdrawn from the at least one initial stage reactor and renewed as described above will be introduced into both the at least one intermediate stage reactor and the final stage reactor, catalyst withdrawn from the final stage reactor will be recycled to the at least one intermediate stage reactor and the catalyst withdrawn therefrom will be introduced into the at least one initial stage reactor. Preferably, the catalyst withdrawn from either or both of the final stage reactor and the at least one intermediate stage reactor will be enhanced as described above before being introduced into the next lower stage reactor. Catalyst withdrawn from the at least one initial stage reactor and renewed may be partially recycled thereto as well. While other permutations of recycle can be contemplated herein, those described are of maximum practical value and are preferred.

The system provided in accordance with the present invention comprises a plurality of reactors consisting of at least one initial stage reactor and a final stage reactor operably connected in series such that the synthesis gas is introduced into the at least one initial stage reactor and the effluent therefrom introduced into the final stage reactor. The system includes means for withdrawing a mixture of hydrocarbons and a portion of the catalyst from the at least one initial stage reactor and treating the catalyst to renew, or renew and enhance, it and at least partially returning it to the at least one initial stage reactor. The system may also include means for recycling treated catalyst between the at least one initial stage reactor and the final reactor stage reactor. The system is advantageous in that it facilitates a more efficient use of the catalyst at each stage, and increases the efficiency of conversion of the synthesis gas to the desired products. The system of the invention also facilitates the use of different types of catalysts within the process to take advantage of the unique properties of each to more efficiently carry out the synthesis. It will appreciate that various modifications of the system as described above can be carried out without departing from the scope of the invention. Such art-recognized modifications are to be considered within the scope of the present invention.

What is claimed is:

1. A process for the catalytic hydrogenation of carbon monoxide to form a mixture of hydrocarbons in a plurality of reactors operably connected in series comprising introducing a feed gas comprising carbon monoxide and hydrogen into at least one initial stage reactor and introducing the effluent therefrom into a final stage reactor so that unconverted feed gas is reacted therein, wherein the catalyst in the at least one initial stage reactor is a Dispersed Metal Catalyst (DAM) and is not immobilized, said catalyst comprising one or one or more members selected from the group consisting of Group VIII metals and copper and the catalyst in the final stage reactor is the same as or different from that in the initial stage reactor, said process additionally including the steps of:

a) withdrawing a mixture comprising hydrocarbons and a portion of said catalyst from the at least one initial stage reactor during operation thereof:

b) treating said catalyst mixture to reduce the hydrocarbon content thereof;

c) heating the resulting mixture in a non-oxidizing atmosphere to a temperature above the melting temperature of at least one of said metals thereby substantially removing non-metallic impurities therefrom and forming a slag of any refractory metal oxides therein on the resulting melt;

d) removing the slag, if present;

e) cooling the melt to solidify it;

f) treating the solid to reduce the particle size thereof to a fine powder of renewed catalyst; and g) returning at least a portion of the catalyst to said at least one initial stage reactor.

2. A process in accordance with claim 1, wherein the particle size of the solid formed in step e) is reduced by a plurality of hydrogen absorption/desorption cycles.

3. A process in accordance with claim 1, wherein the DAM catalyst is a Raney catalyst, said process additionally including the steps of adding a leachable metal selected from the group consisting of aluminum, titanium, silicon or zinc to the reduced hydrocarbon mixture formed in step b) or the melt formed in step c), and the solid formed in step e) is reduced to a fine powder of renewed catalyst by physical comminuting to reduce the particle size followed by chemical extraction or dissolution of said leachable metal.

4. A process in accordance with claim 1, wherein the effluent from the at least one initial stage reactor is treated to remove liquids therefrom prior to being introduced into the final stage reactor.

5. A process in accordance with claims 1 or 3, further including the step of modifying or enhancing the activity of the renewed catalyst by adding one or more metals selected from the group consisting of Re, Ru, Co, Pt, Pd, Mo, W, Cr, Ni, Mg, Zr, Hf, Mn, Fe, Cu and Ce to the reduced hydrocarbon mixture formed in step b) or the melt formed in step c).

6. A process in accordance with claims 1 or 3, wherein the catalyst mixture withdrawn from the at least one initial stage reactor is treated to reduce the hydrocarbon content thereof by one or a plurality, in any sequence, of the following steps:

gravitational or centrifugal separation of the catalyst particles from the hydrocarbons and decanting the hydrocarbons therefrom;

filtration of the mixture;

treating the mixture with a solvent or supercritical fluid that weakens the interaction between the particles and the hydrocarbons, followed by separation of the liquid and solid phases;

contacting the mixture with a hydrogen-containing gas at a temperature above that required for the carbon monoxide hydrogenation; and contacting the mixture with an oxygen-containing gas or steam at elevated temperature.

7. A process in accordance with claims 1 or 3, wherein catalyst is returned to the at least one initial stage reactor by one or more of:

forming a slurry of the catalyst with liquid hydrocarbons and introducing said slurry into the reactor;

forming a suspension of the catalyst in a non-oxidizing gas and introducing said suspension into the reactor; and transferring the catalyst to the reactor by gravity or pressure gradient.

8. A process in accordance with claims 1 or 3, wherein, prior to being returned to the at least one initial stage reactor, the activity of the catalyst is further enhanced by a process comprising:

forming a slurry of the catalyst particles in a suitable liquid;

contacting the catalyst with an oxidizing agent at temperatures below 200° C. thereby forming an oxidized catalyst precursor comprising metals and at least one of hydroxides thereof and oxides thereof, and reducing said oxidized catalyst precursor with a hydrogen-containing gas at a temperature above about 200° C.

9. A process in accordance with claim 8, wherein, prior to being reintroduced into the at least one initial stage reactor, the catalyst is passivated by:
treatment with a carbon monoxide-containing gas under conditions such that the carbon monoxide is not significantly decomposed; or
treatment with a gas containing carbon monoxide and hydrogen under conditions such that the carbon monoxide is not significantly hydrogenated.

10. A process in accordance with claims 1 or 3, wherein at least a portion of the hydrocarbons formed are upgraded to more valuable products by at least one of fractionation and conversion operations.

11. A process in accordance with claims 1 or 3, wherein the catalyst in said final reactor is a DAM catalyst, at least a portion of the renewed catalyst formed in step f) is introduced into said final stage reactor and said DAM catalyst is withdrawn from the final stage reactor and introduced into the at least one initial stage reactor.

12. A process in accordance with claim 11 additionally including enhancing the catalyst prior to introducing it into the at least one initial stage reactor by:
forming a slurry of the catalyst particles in a suitable liquid;
contacting the catalyst with an oxidizing agent at temperatures below 200° C. thereby forming an oxidized catalyst precursor comprising metals and at least one of hydroxides thereof and oxides thereof, and
reducing said oxidized catalyst precursor with a hydrogen-containing gas at a temperature above about 200° C.

13. A process in accordance with claim 1, wherein the effluent withdrawn from said at least one initial stage reactor is introduced into at least one intermediate stage reactor so that unconverted feed gas is further reacted therein, and the effluent from said at least one intermediate reactor is introduced into said final stage reactor.

14. A process in accordance with claim 13, wherein the effluent from both of the at least one initial stage reactor and the at least one intermediate stage reactor are treated to remove liquids therefrom prior to being introduced into the next succeeding stage reactor.

* * * * *